United States Patent [19]

Miller et al.

[11] 4,121,594

[45] Oct. 24, 1978

[54] TRANSCUTANEOUS ELECTRICAL NERVE STIMULATOR

[75] Inventors: Curtis H. Miller, Burnsville; Mark R. Kaldun, St. Paul; Robert A. Arp, Eden Prairie, all of Minn.

[73] Assignee: Med General, Inc., Minneapolis, Minn.

[21] Appl. No.: 836,703

[22] Filed: Sep. 26, 1977

[51] Int. Cl.² ............................................. A61N 1/36
[52] U.S. Cl. .................................................... 128/422
[58] Field of Search ................... 128/419 R, 421, 422

[56] References Cited

U.S. PATENT DOCUMENTS

| | | | |
|---|---|---|---|
| 2,622,601 | 12/1952 | Nemec | 128/422 |
| 3,503,403 | 3/1970 | Yarger | 128/421 |
| 3,518,996 | 7/1970 | Cortina | 128/422 |
| 3,589,370 | 6/1971 | McDonald | 128/422 |
| 3,612,060 | 10/1971 | Colyer | 128/422 |
| 3,624,484 | 11/1971 | Colyer | 128/422 |
| 3,794,022 | 2/1974 | Nawracaj et al. | 128/422 |
| 3,817,254 | 6/1974 | Maurer | 128/421 |
| 3,835,833 | 9/1974 | Limoge | 128/422 |
| 3,885,573 | 5/1975 | Hara | 128/421 |
| 3,888,261 | 6/1975 | Maurer | 128/421 |
| 3,893,462 | 7/1975 | Manning | 128/421 |
| 3,894,532 | 7/1975 | Morey | 128/422 |
| 3,895,639 | 9/1975 | Rodler | 128/422 |
| 3,958,577 | 5/1976 | Rodler | 128/422 |
| 3,983,881 | 10/1976 | Wickham | 128/421 |
| 4,014,347 | 3/1977 | Halleck et al. | 128/422 |
| 4,062,365 | 12/1977 | Kameny | 128/422 |

FOREIGN PATENT DOCUMENTS 2,109,085 9/1971 Fed. Rep. of Germany ........... 128/422

Primary Examiner—William E. Kamm
Attorney, Agent, or Firm—Orrin M. Haugen; Thomas J. Nikolai

[57] ABSTRACT

A transcutaneous electrical nerve stimulator in which a unijunction transistor relaxation oscillator is used to produce variable frequency, variable width pulses. The relaxation oscillator drives a two stage transistor amplifier and the output therefrom is transformer coupled to a set of output electrodes which are adapted to be placed on the area of a patient to be treated. The amplitude of the signals applied to the patient as well as the rate and duration thereof are controllable so that the patient may adjust the nerve stimulation to suit his particular needs.

2 Claims, 3 Drawing Figures

TRANSCUTANEOUS ELECTRICAL NERVE STIMULATOR

BACKGROUND OF THE INVENTION

I. Field of Invention

This invention relates generally to electro-medical apparatus and more specifically to a transcutaneous electrical nerve stimulator which may be used to inhibit the transmission of pain impulses from the peripheral to the central nervous system.

II. Description of Prior Art

It is well known that the application of electrical stimulation to the body of a patient in the area of soreness or pain can have a therapeutic and anesthetizing effect, although the physiological basis is not completely understood. As is set forth in the Limoge U.S. Pat. No. 3,835,833, the application of electrical signals at electrodes placed at suitably chosen points on the body of a patient is capable of causing various therapeutic effects such as local anesthesia or relaxation of muscles and nerves. There are described in the prior art various electronic circuits for selectively applying electrical impulses of variable amplitude, frequency and duration. It is also recognized that the application of electrical stimulation can be accompanied by discomforting sensation such as a burning sensation, stinging or prickling. Further, it is known that the ability of a nerve cell to respond to a stimulus of given current magnitude is related to the duration of time during which the current impulse flows. This is often expressed graphically as a "Strength-Duration Curve". Thus, a reduction in time duration may be compensated for by an increase in current amplitude.

SUMMARY OF THE INVENTION

The present invention provides a new and improved design of a transcutaneous nerve stimulator which is characterized by small size, low power consumption, and simplicity of adjustment of the electrical output in amplitude, duration and repetition rate such that it may be easily worn and operated by the patient without the need for direct medical supervision following the initial perscription and application training.

In the implementation of the present invention, a battery powered relaxation type oscillator employing a unijunction transistor as its active element is used to generate pulses which may be varied in frequency and pulse duration by potentiometer type controls. The pulses from the relaxation oscillator are amplified and transformer coupled to output jacks to which the body stimulating electrodes may be attached. Associated with the secondary windings of the transformer are further potentiometer controls for adjusting the amplitude of the currents applied to the body by way of the electrodes. Thus, the patient is permitted to choose the point on the Strength-Duration Curve so as to minimize the discomforting side effects.

DETAILED DESCRIPTION OF A PREFERRED EMBODIMENT

Figure 1:
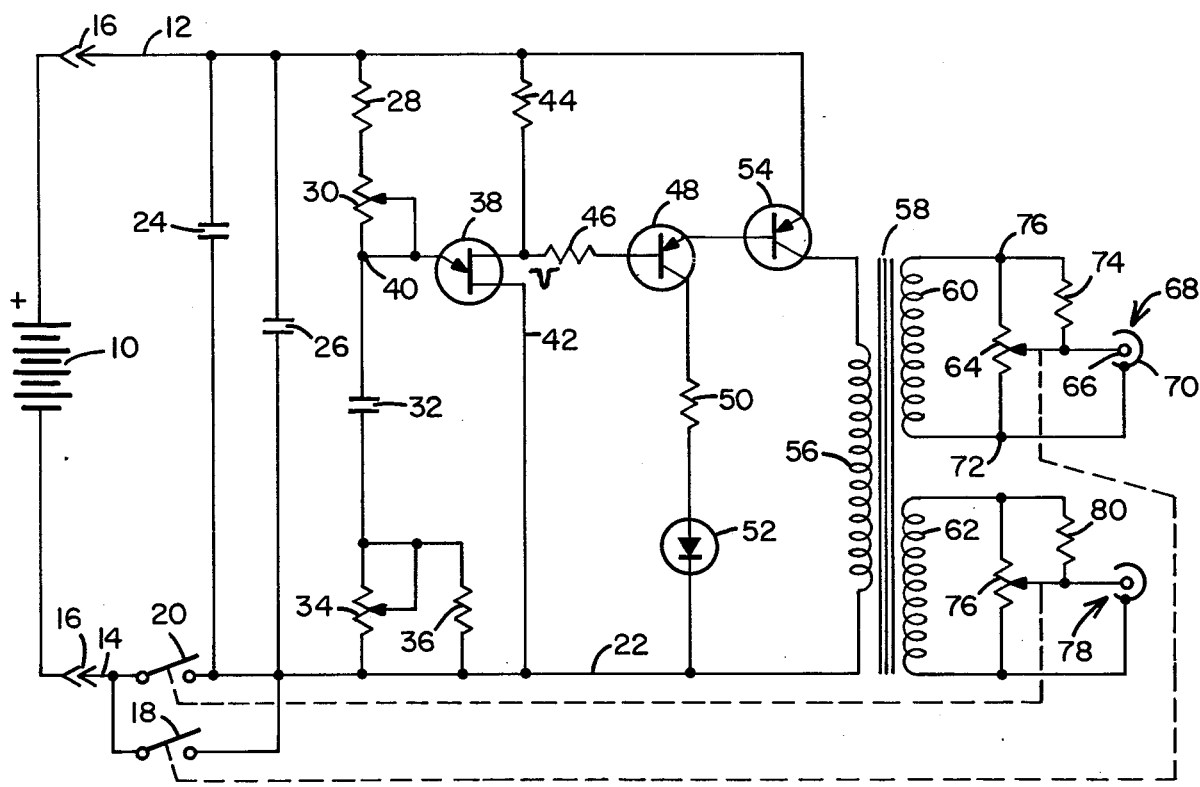
FIG. 1 is an electrical schematic diagram of a transcutaneous stimulator embodying the present invention.

Referring first to FIG. 1, there is shown a direct current power source in the form of a rechargeable battery pack 10 which is connected to a positive bus 12 and a negative bus 14 by way of contacts 16. First and second single pole single through on/off switches 18 and 20 are connected in parallel with one another and in series between the negative bus 14 and a conductor 22. Connected in parallel with one another and between the positive bus 12 and the conductor 22 are first and second capacitors 24 and 26 which serve to reduce the peak current surge from the battery pack 10, thereby preventing premature battery deterioration.

Connected in a series relationship between the positive bus 12 and the conductor 22 are a resistor 28, a potentiometer 30, a capacitor 32 and an additional potentiometer 34. Connected in parallel with the potentiometer 34 is a fixed resistor 36.

A unijunction transistor 38 has its emitter electrode, E, connected to a junction point 40 between the potentiometer 30 and the capacitor 32. The emitter electrode of the uni-junction transistor is also connected to the wiper arm of the potentiometer 30. The base 1 electrode, B1, of the unijunction transistor 38 is connected by a conductor 42 to the conductor 22 while the base 2 electrode, B2, is coupled through a resistor 44 to the positive bus 12.

The base 2 electrode is also coupled through a resistor 46 to the base electrode of a PNP transistor 48. The collector electrode of this transistor is coupled through a resistor 50 and a light emitting diode (LED) 52 to the conductor 22.

The emitter electrode of transistor 48 is connected directly to the base electrode of a PNP transistor 54 whose emitter is connected to the positive bus 12. The collector electrode of transistor 54 is connected to a first terminal of the primary winding 56 of a transformer 58 and the remaining primary winding terminal is connected to conductor 22.

The transformer 58 is preferably a bifilar-wound device having first and second secondary windings 60 and 62. Connected directly across the secondary winding 60 is a potentiometer 64 whose wiper arm is connected to a first contact 66 of a conventional coaxial jack identified generally by numeral 68. The other terminal 70 of the jack 68 is connected to the outer terminal 72 of the potentiometer 64. A fixed resistor 74 has one lead connected to the wiper arm of the potentiometer 64 and its remaining lead connected to a junction 76 which is the common point between the upper terminal of the secondary winding 60 and the remaining outer terminal of the potentiometer 64.

In a similar fashion, a potentiometer 76 is connected by its outer terminals across the secondary winding 62 of transformer 58 with the wiper arm thereof connected to a first contact of a coaxial jack type connector 78 with a resistor 80 being connected between the wiper arm of the potentiometer and the upper terminal of the potentiometer 76. The remaining contact of the jack 78 is connected to the lower terminal of the potentiometer 76. Now that the circuit arrangement has been described in detail, consideration will be given to its mode of operation.

OPERATION

When either switch 18 or switch 20 is closed, a current flows from the rechargeable battery pack 10 and through capacitors 24 and 26 to charge them to substantially battery potential. A current also flows through resistor 28, potentiometer 30, capacitor 32 and the parallel combination of potentiometer 34 and resistor 36 causing the capacitor 32 to charge up exponentially at a rate determined by the product of the total series resistance in ohms and the value of capacitor 32 in farads. As the capacitor 32 charges, a point is reached where the emitter voltage of the unijunction transistor 38 exceeds its peak point voltage $V_p$ and the emitter becomes forward biased. This, in turn, causes the dynamic resistance between the emitter electrode and the base 1 electrode to drop to a low value and the capacitor 32 rapidly discharges through the emitter and base 1 electrode of the unijunction transistor 38 and the parallel combination of the potentiometer 34 and the fixed resistor 36. When the emitter voltage at junction 40 reaches a value of approximately 2 volts, the emitter ceases to conduct and the cycle is repeated. By adjusting the position of the wiper arm of potentiometer 30, the rate at which the capacitor 32 charges can be varied and thus the rate of oscillation of the relaxation oscillator. By adjusting the position of the wiper arm on the potentiometer 34, it is possible to control the pulse width of the oscillator output signal.

When the unijunction transistor 38 is driven into conduction, a current is drawn through the positive bus 12, through the resistor 44 and the base 2 to base 1 electrodes of the unijunction transistor 38 causing a negative going impulse to appear at the junction point between resistor 44 and resistor 46. This negative pulse is applied through the resistor 46 to the base electrode of PNP transistor 48 causing transistor 48 to be forward biased. A current path is thus established from the positive plate of the capacitors 24 and 26, through the positive bus 12, the emitter to base path of transistor 54 and from the emitter to collector path of the transistor 48. This current flows through the resistor 50 and the LED 52 causing the LED to blink on and off at the oscillation rate of the unijunction transistor relaxation oscillator.

The flow of current in the emitter to base path of transistor 54 also causes this transistor to be forward biased such that a low impedance is presented between its base and collector electrodes. Hence, a substantial current flows from the battery 10 and the capacitors 24 and 26 through the primary winding 56 of transformer 58 to thereby induce voltage signals in the secondary windings 60 and 62 of the transformer 58. It is to be noted that the switches 18 and 20 are mechanically coupled to the potentiometers 64 and 76, much like the on/off switch and volume control of a typical radio receiver. By positioning the wiper arms of the potentiometer 64 and 76, it is possible to control the amplitude of the voltage or current signal applied to the coaxial jack 68 and 78. If switch 18 is open, the wiper arm of the potentiometer 64 is in its lower most position so that the contacts 66 and 70 of the jack 68 are effectively shorted. The same holds true for the switch 20. However, as the shaft on which the switch 18 or 20 is rotated, the wiper arms of the associated potentiometers 64 and 76 are moved upward, thereby increasing the amplitude of the output signal applied across the contacts of the jacks 68 and 78. Of course, if both switches 18 and 20 are open, the battery 10 is disconnected from the remainder of the circuit and no power is delivered to the relaxation oscillator or to the output.

Figure 2:
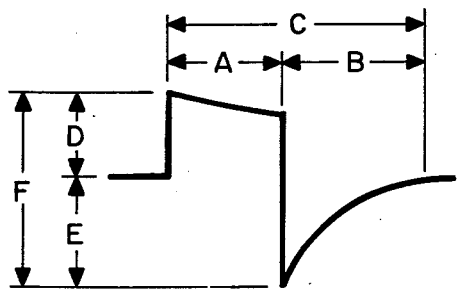
FIG. 2 is a waveform of the output signals applied to the patient.

FIG. 2 illustrates the wave form of the output signal appearing across the terminals of the jacks 68 and 78 when their associated on/off switches 18 and 20 are closed. It will be observed that the output signal is asymmetrical and biphasic in nature. This wave form produces maximum stimulating power for the least possible battery drain and has been subjectively reported to be the most comfortable and to have the least potential for irritation.

With no limitation intended, it is deemed beneficial for a full understanding of the operation of the preferred embodiment to set forth typical component values which may be utilized in the implementation of the preferred embodiment.

TABLE I

| | |
|---|---|
| $C_{24}$, $C_{26}$ | 180 uf |
| $C_{32}$ | 0.47 uf |
| $R_{28}$ | 22k ohms |
| $R_{30}$ | 220k ohms variable |
| $R_{34}$ | 100 ohms variable |
| $R_{36}$ | 82 ohms |
| $R_{44}$, $R_{74}$, $R_{80}$ | 1k ohms |
| $R_{46}$ | 470 ohms |
| $R_{50}$ | 47 ohms |
| $R_{64}$, $R_{76}$ | 10k ohms variable |
| Unijunction 38 | Type 2N2647 |
| Transistors 48 & 54 | Type MJE371 |
| LED 52 | Type FLV 111 |
| Battery 10 | 5 volt-rechargeable |

With the component values as set forth above the parameters associated with the wave form of FIG. 2 are as follows:

TABLE II

| Pulse Parameter | 510 Ohm Load Min. | 510 Ohm Load Max. | 1k Ohm Load Max. |
|---|---|---|---|
| Amplitude (F) | 0 | 65v | 85v |
| (D) | 0 | 20v | 25v |
| (E) | 0 | 45v | 60v |
| Current - Peak | 0 | 65ma | 85ma |
| - Ave. | 0 | .55ma | .71ma |
| Frequency | 10Hz. | 100Hz. | 100Hz. |
| Width (C) | 120μsec | 200μsec | 200μsec |
| (A) | 60μsec | 140μsec | 140μsec |
| (B) | 60μsec | 60μsec | 60μsec |

It is to be understood that the values set forth in Table II between minimum and maximum depend on the control settings.

Figure 3:
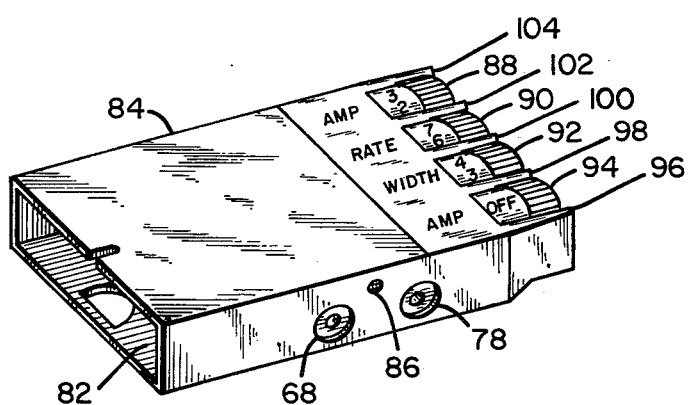
FIG. 3 is a pictorial view of the physical construction of the device.

In FIG. 3, there is shown an illustration of a transcutaneous electrical nerve stimulator package. The rectangular opening 82 is adapted to receive a rechargeable battery pack and contained within the housing 84 are the electrical contacts 16 of FIG. 1. Hence, when the battery pack is inserted into the receptacle 82 contact is made between the battery terminals and the power input terminals of the stimulator unit. The jacks 68 and 78 are mounted on the side of the housing 84 and a small aperture 86 is provided for viewing the light emitting diode 52 in FIG. 1. At the right end of the package are a plurality of manually rotatable knobs 88, 90, 92 and 94. Formed integrally in the housing 84 are projecting fingers 96 through 104 whose height dimensions are slightly greater than the diameter of the knobs 88 through 94. Hence, the knobs will not be inadvertently or accidentally rotated if brushed. The knob 88 controls an on/off switch such as switch 18 in FIG. 1 and further rotation thereof adjusts the potentiometer 64 in FIG. 1. Similarly, the knob 94 controls the on/off positioning of switch 20 and controls its associated potentiometer 76.

Knob 90 controls the setting of the potentiometer 30 and therefore the rate of oscillation. Knob 92 controls the potentiometer 34 and therefore the pulse width of the output signal.

The transcutantous electrical nerve stimulator package of FIG. 3 may typically be 6.75 centimeters in length, 4.67 centimeters in width and having a thickness of 1.67 centimeters. Its weight with a rechargeable battery pack in place may be in the range of 60 to 100 grams. Thus, the device is extremely portable, easy to operate and provides an adjustable output which the patient himself may control for optimum performance.

While there has been described and pointed out the fundamental novel features of the invention as applied to a preferred embodiment thereof, it will be understood that various omissions and substitutions in changes in the form and details of the device illustrated and their operation may be made by those skilled in the art, without departing from the spirit of the invention. It is the invention, therefore, to be limited only as indicated by the scope of the following claims.

What is claimed is:

1. A portable transcutaneous electrical nerve stimulator adapted to apply electrical stimulating pulses to the body of a patient by way of body contacting surface electrodes, comprising in combination:
   (a) a source of direct current potential having first and second terminals;
   (b) oscillator means including
      (1) a unijunction transistor having first and second base electrodes respectively coupled to said first and second terminals of said source of direct current potential and an emitter electrode,
      (2) a timing circuit including first and second variable resistors and a capacitor connected between said first and second variable resistors, said timing circuit connected in series between said first and second terminals of said source of direct current potential, and
      (3) means connecting said emitter electrode of said unijunction transistor to the connection between said first variable resistor and said capacitor;
   (c) semiconductor amplifier means including
      (1) first and second transistors, each having an emitter electrode, a collector electrode and a base electrode, the base electrode of said second transistor being connected to the emitter electrode of said first transistor and the emitter electrode of said second transistor being coupled to said first terminal of said source of direct current potential,
      (2) a light emitting diode coupled between said collector electrode of said first transistor and said second terminal of said source of direct current potential, and
      (3) means coupling the base electrode of said first transistor to said second base electrode of said unijunction transistor; and
   (d) output means including,
      (1) a pulse transformer having a primary winding and at least one secondary winding,
      (2) means connecting said primary winding of said pulse transformer between said collector electrode of said second transistor and said second terminal of said source of direct current potential,
      (3) jack means adapted to be connected to said surface electrodes, and
      (4) a variable voltage divider coupled between said secondary winding of said pulse transformer and said jack means,
   the arrangement being such that biphasic, asymmetrical pulses of adjustable frequency, pulse width and pulse amplitude may be applied to the body of the patient, said frequency being determined by said first variable resistor, said pulse width being determined by said second variable resistor and said pulse amplitude being determined by said variable voltage divider.

2. Apparatus as in claim 1 and further including a single pole, single throw switch connected in series with said source of direct current potential for selectively connecting or disconnecting said source to or from said oscillator means.

* * * * *